United States Patent [19]
Williams

[11] 3,950,792
[45] Apr. 20, 1976

[54] MASTECTOMY ACCESSORY FOR BRA

[76] Inventor: Marguerite R. Williams, 500 Plattsville Road, Trumbull, Conn. 06611

[22] Filed: Feb. 7, 1975

[21] Appl. No.: 548,161

[52] U.S. Cl. .................................. 3/36; 128/478
[51] Int. Cl.² ........................ A61F 1/00; A41C 3/10
[58] Field of Search ............ 3/36; 128/462, 478–481

[56] References Cited
UNITED STATES PATENTS

| | | | |
|---|---|---|---|
| 2,953,133 | 9/1960 | Seller | 3/36 X |
| 3,173,420 | 3/1965 | Mazzoni et al. | 128/478 |
| 3,568,681 | 3/1971 | Comollo | 3/36 X |
| 3,651,522 | 3/1972 | Bernfeld | 3/36 |
| 3,701,168 | 10/1972 | Balow | 3/36 |

Primary Examiner—Ronald L. Frinks
Attorney, Agent, or Firm—Wood, Herron & Evans

[57] ABSTRACT

An accessory which can be incorporated into a conventional bra at the time of manufacture or added subsequent thereto for conversion thereof to a mastectomy bra. The accessory hides variable amounts of scar tissue or other type of chest disfigurement in the region where the breast has been removed, by means which may be adjusted by the wearer, the area hidden depending in amount and location upon the nature and extent of the mastectomy, i.e., removal of all or a part of one or both breasts with or without removal of adjacent muscle tissue and/or lymph nodes. The resultant mastectomy bra functions to contain in each cup one or more breast prostheses in cases where both natural breasts have been removed, or where only one breast has been removed to support a natural breast in conventional fashion in one cup and one or more prostheses in the other cup, while maintaining a harmonious and apparently similar appearance on both the left and right sides thereof, while covering both the mastectomy area and the normal breast in a visually similar manner.

18 Claims, 12 Drawing Figures

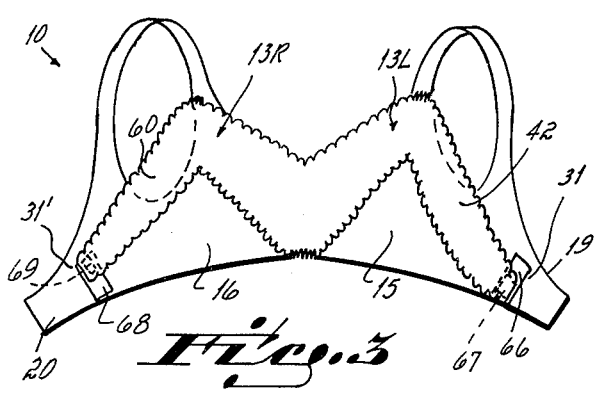
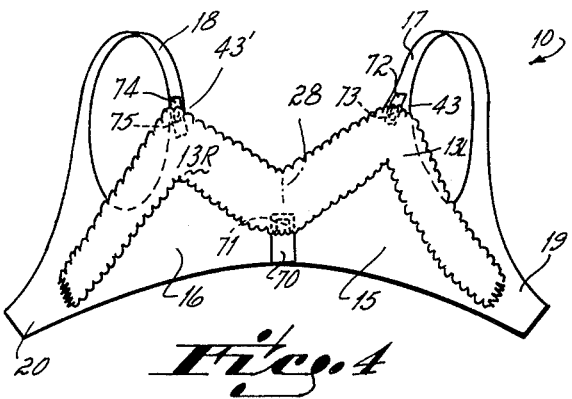
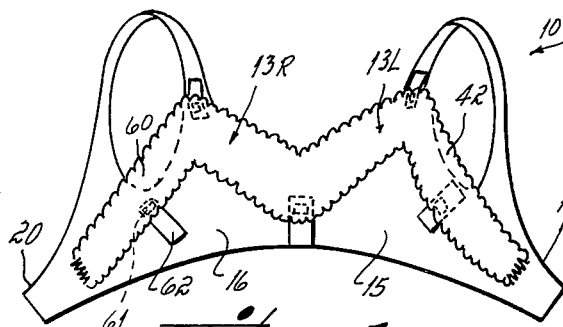
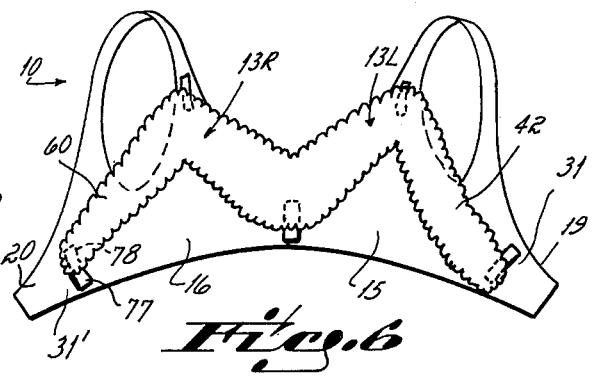
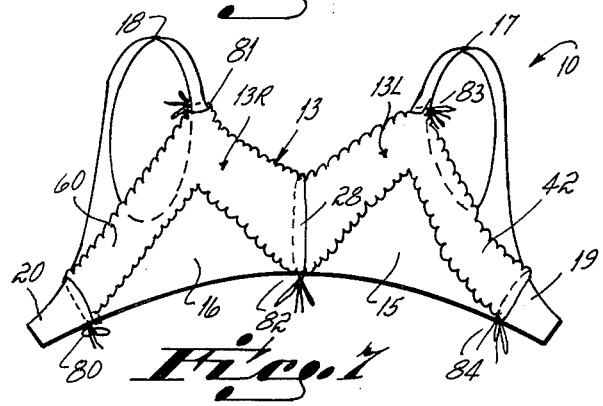
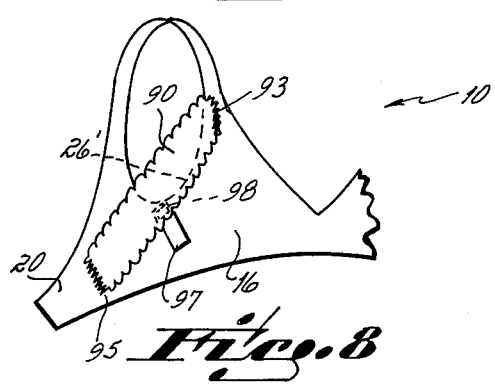
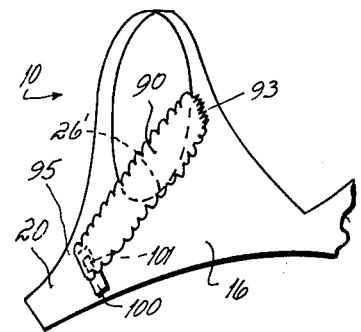
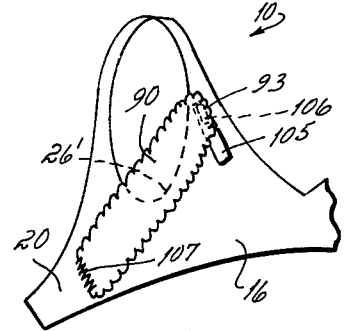
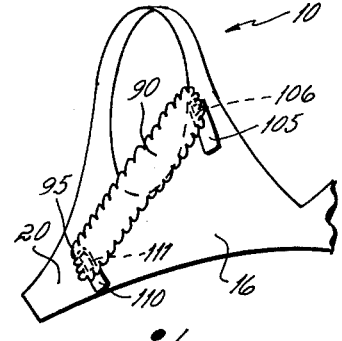

MASTECTOMY ACCESSORY FOR BRA

This invention relates to a mastectomy bra, and more particularly to an accessory for converting a conventional bra into a bra suitable for a mastectomy patient.

Mastectomy operations vary from patient to patient. Such operations may involve removal of the left, right or both breasts, as well as removal of the surrounding muscle tissue and/or the lymph nodes situated under the arms. Some patients undergo removal of all of the foregoing, others less.

Subsequent to recovery from surgery, the mastectomy patient is faced with the problem of reconstructing as close an approximation as possible to the original chest and/or underarm configuration. Such is important for physical, psychological and aesthetic reasons. To accomplish this, the patient selects one or more prosthetic devices depending on the nature and extent of the operation. For example, if a single breast and substantial surrounding muscle tissue and lymph nodes have been removed, multiple artificial breast forms, prostheses, and/or pads may be needed. In addition, the patient must select a mastectomy bra to contain and position the prosthetic device(s), as well as support in conventional fashion a natural breast if both breasts have not been removed.

Typically, the mastectomy bra includes a pocket in one or both of the cups into which the prosthesis is inserted. The pocket configuration approximates that of the cup, which in turn approximates that of the natural breast being reconstructed. In practice, due to operations of varying severity, i.e., involving removal of varying amounts of surrounding muscle and/or lymph nodes, the size and shape of the prosthesis required by different patients can vary even though the size of the natural breast being reconstructed is the same. As a consequence, patients having the same size natural breast, but with operations of different severity, frequently end up with a bra not specifically designed to accomodate their particular problem.

For example, a mastectomy bra designed to accomodate multiple and/or large prostheses devices due to removal of substantial amounts of muscle tissue and the like, while fitting those patients with very extensive surgery, will be inappropriate for others with less extensive surgery. In addition, such a bra will be much too large for the patient's normal breast in cases where both breasts have not been removed. Also, where a natural breast remains, the upper region of the bra surrounding the natural breast will be too high and bind the underarm uncomfortably. Similarly, a mastectomy bra which is made to fit comfortably over a patient's one remaining normal breast, will not be high enough and/or large enough on the other side where the breast has been removed to contain the prostheses and hide the scarred and disfigured chest and underarm area.

In the past, in order to adapt standard mastectomy bras to the individual need of patients, it has often been necessary to modify the bra. In some cases, the modification includes adding sections of material to the bra to cover breast pads and the like which are too large to fit in the existing breast cup pocket of the bra. This gives the bra a patched-up and unsightly appearance. In addition, the patient does not have the psychological satisfaction of wearing a pretty and new article of clothing. A further disadvantage is that the adjustment to the bra is typically made by a fitter, which is costly and involves an invasion of the patient's privacy. Moreover, competent fitters are in short supply and retail stores face difficulty in staffing their operations.

In summary, mastectomy bras on the market today invariably give the appearance of a strictly functional and surgical-appearing garment, devoid of any aesthetic, pretty and feminine appeal so desired by women in general and in particular by women having suffered the traumatic experience of losing one or both breasts. Moreover, they are not self-adjustable to the individual needs of the wearer, but require unsightly modifications, often by fitters who are difficult to obtain and invade the user's privacy.

It is therefore an objective of this invention to provide a mastectomy bra which can contain one or more prostheses in the region of either or both breasts, support a natural breast if one remains, and hide varying degrees of scar tissue or other chest disfigurement, all in dependence upon the individual needs of the wearer. This objective has been accomplished by designing a mastectomy accessory, which can be incorporated in a conventional bra at the time of manufacture or added thereafter, having 1. an adjustable overlay which can be variably positioned by the user to hide varying amounts of scar tissue or other disfigurement on one or both sides of the chest and underarm region, and
2. an underlay which in combination with the cup and underarm panel of the bra serves as a pocket to contain one or more prostheses of varying size and shape or alternatively serves as a liner for the cup to support a natural breast in normal fashion where such has not been removed.

Thus, the adjustable mastectomy accessory of this invention does not affect the basic breast-supporting purpose of the bra, but acts in an independent manner to cover and contain to varying degrees the traumatized region of the chest having one or more breast prostheses while covering a normal breast in standard fashion should such remain. The result is an aesthetically pleasing garment which may be adjusted by the wearer without the aid of a fitter to accomodate the wearer's individual need for coverage of disfigured chest and underarm regions, containment of one or more prosthetic devices, and/or support of a natural breast.

In a preferred form of the invention, the overlay is located along the upper edge of the bra in the region of the cups and underarm, and is provided with adjustable fasteners to variably position it in a vertical direction to cover more or less of the chest or underarm depending on the location and extent of scar tissue or other disfigurements occasioned by the mastectomy. In the preferred embodiment, the underlay, which in combination with the cup and underarm panel of the bra, defines a pocket into which one or more prostheses can be placed and/or a normal breast supported in conventional manner, is provided with a flap along the upper edge thereof which can be folded selectively in variable amounts to contain different size prostheses.

Of course, it should be understood that the overlay structure can function without the underlay which, with the bra cup, defines a pocket. For example, such an overlay structure might be added to a standard manufactured bra already containing a prosthesis pocket of a different design; or, it might be determined in manufacturing that a different design of underlay prosthesis pocket might be preferred over that described in connection with the present invention. Also, some prostheses, such as the silicone ones, do not require pockets in the bra to hold the prostheses, as they are inserted between the bra and the body proper. In such situations, although the bra has no pockets, the overlay of this invention can be used to hide scar tissue, etc. Where the pocket is used, but the surgery is not radical, the prosthesis pocket would not need to extend beyong the upper underarm edge of the bra, and therefore the foldable extension, or flap, of the underlay pocket would not be necessary. However, the overlay would be needed to cover the scar tissue, etc. resulting from the operation.

In one form of the invention, the overlay structure may be made of more or less straight bands of material applied to outer sides of both cups of the brassiere, as well as the underarm regions adjacent each cup, and may be manufactured in such a manner that it may be applied to a standard or conventional bra, either by sewing the overlay to the conventional bra after it has been manufactured or incorporating it into the bra at the time of manufacture. Alternatively, the overlay may be an M-shaped structure applied to the complete upper configuration of the garment, including that portion above both cups and above the underarm area adjacent each cup, and may be incorporated in the garment at the time of manufacture or thereafter. Finally, the adjustable means used to raise or lower the overlay structure in relation to the bra cup and underarm regions can be one of many systems of fasteners well known in the art, such as Velcro, hooks and eyes, snaps, buttons, etc.

These and other advantages and features of the invention will be more readily apparent from a detailed description of the drawings thereof in which:

FIG. 3 is a front elevational view of the outside of another embodiment of the invention;

FIG. 4 is a front elevational view of the outside of another embodiment of the invention;

FIG. 5 is a front elevational view of the outside of another embodiment of the invention;

FIG. 6 is a front elevational view of the outside of another embodiment of the invention;

FIG. 7 is a front elevational view of the outside of another embodiment of the invention;

FIG. 8 is a front elevational view of the outside of a portion of another embodiment of the invention;

FIG. 9 is a front elevational view of the outside of a portion of another embodiment of the invention;

FIG. 10 is a front elevational view of the outside of a portion of another embodiment of the invention; and FIG. 11 is a front elevational view of the outside of a portion of another embodiment of the invention.

To facilitate a complete understanding of the mastectomy accessory of this invention, the mastectomy accessory is described in connection with its use as an adjunct to a conventional brassiere or bra. However, it is to be understood that the mastectomy accessory of this invention can be used with any type of breast-supporting or breast-covering garment, including but not limited to, a long-line brassiere, corselette, leisure brassiere, lingerie, or lounge wear.

Figure 1:
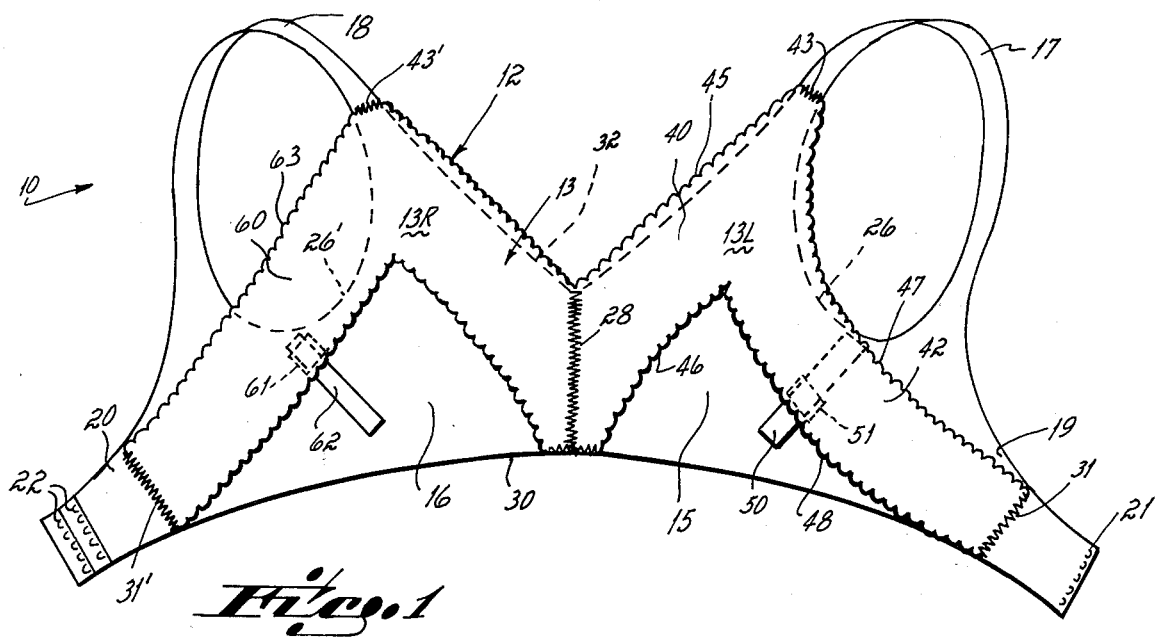
FIG. 1 is a front elevational view of the outside of a preferred embodiment of the invention.
Figure 2:
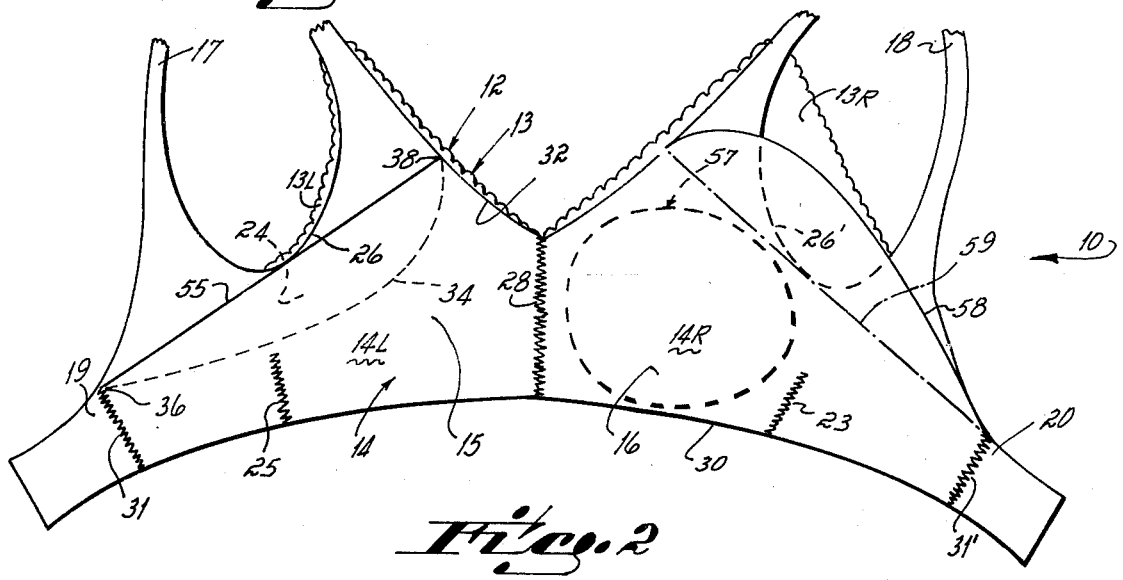
FIG. 2 is a rear elevational view of the inside of the embodiment of the invention depicted in FIG. 1.

FIGS. 1 and 2 show the outside and inside, respectively, of a conventional bra 10 incorporating the mastectomy accessory 12 of this invention which includes an overlay 13 and an underlay 14. The bra 10, which may be of any conventional design, includes left and right cup sections 15 and 16 for covering and supporting the left and right breasts of the wearer when such have not been removed by a surgical procedure or mastectomy. Connected to the cup sections 15 and 16 in the upper region thereof are shoulder straps 17 and 18. Shoulder straps 17 and 18, preferably adjustable in length, also connect to the upper region of the left and right back sections 19 and 20 of the bra 10. Back sections 19 and 20 are provided with suitable fasteners 21 and 22, permitting the bra to be secured in encircling relation about the chest of the wearer. The back sections 19 and 20 pass underneath the arms of the wearer when the bra is worn, joining the cups 15 and 16 in front. The cups 15 and 16, which essentially constitute the front of the bra 10, and the back sections 19 and 20, which basically form the rear of the bra, may be fabricated of a single molded or contoured piece of material, or of multiple panels stitched together in conventional fashion.

The mastectomy accessory 12, as noted, includes an overlay 13 and an underlay 14. With reference to FIG. 2, the underlay 14 includes left and right sections or panels 14L and 14R. Since panels 14L and 14R are mirror images of each other, only left underlay section 14L is described in detail. Left underlay panel 14L is generally co-extensive with the left cup 15 and the major portion of the left back section 19, except for the inclusion of a flap 24 which extends above the upper edge 26 of the left cup 15 and left back section 19. Left underlay section 14L is stitched to the bra 10 along the central vertical junction line 28 between the cups 15 and 16, along the bottom horizontal edge 30 of the left cup 15 and left back 19, along a vertical edge 31 near the fastener 21, and along a portion of the upper central edge 32 of the left cup 15. The left underlay section 14L is not stitched along the upper edge 34 of the flap 24 between the point designated 36 whereat the strap 17 connects to the left back section 19 and the point designated 38 along the bra cup edge 32, in order to permit insertion of one or more breast prostheses as needed. To retain the prosthesis, such as prosthesis 57, in the desired position within the pocket formed by the underlay section 14R and the bra cup 16, the underlay section 14R and bra cup 16 are stitched together along a vertical line 23. The height of stitch line 23 is not sufficiently high to interfere with flap 58 when it is folded along line 59 and tucked down between the interior of cup 16 and the underlay 14R. A similar stitch line 25 is provided on the left cup 15 and left underlay 14L.

The strap 17, which is adjustable, in combination with the edge 26 of the cup 15 of the bra 10, constitutes an arm-hole for the wearer's left arm.

The overlay 13, as best seen in FIG. 1, includes a left overlay section 13L and a right overlay 13R. Left and right overlay sections 13L and 13R are mirror images of each other, and hence only left overlay section 13L is described in detail. The left overlay section 13L is generally in the form of an inverted "V" having a first section 40 and a second section 42. Section 40 is stitched at its inner end to the bra 10 along the vertical junction line 28 between the cup sections 15 and 16 as well as at its upper most and outer end to the strap 17 at a point 43 where it joins the left cup section 15. The overlay section 42 is stitched at its outer end to the back section 19 along a vertical line 31 as well as at its inner end to the juncture 43 of the strap 17 and left cup 15. The left overlay sections 40 and 42 are not joined to the underlying bra 10 along lines 45, 46 and 47, 48. The position of the left side overlay section 42, particularly the edge 47 thereof, with respect to the arm-hole edge 26 of the cup 15 is, for reasons which will become apparent hereafter, adjustable by means of mating fastener sections 50 and 51, preferably of the Velcro type, which are sewn to the outer surface of the cup 15 and the inner surface of the overlay section 42, respectively.

In use, bra 10, to which the overlay 13 and underlay 14 have been secured in the manner described, is positioned about the chest of the wearer and secured in place with fasteners 21, 22. If the wearer has one natural breast, such as the left breast, it is positioned in the left cup 15, in which case the left underlay section 14L forms a lining for the left cup 15. The flap 24 of the left underlay 14L is folded along line 55 and positioned between the inner surface of the left cup 15 and the remaining portion of the left underlay section 14L. If the patient's natural breast, such as the right breast, has been removed by a mastectomy, a breast prosthesis, such as prosthesis 57, is positioned in the pocket formed by the right underlay 14R and the right cup 16. The flap 58 of the right underlay 14R is not folded along line 59, but is left unfolded to extend upwardly to contain the prosthesis 57. If the prosthesis used is greater in size than prosthesis 57, or a second prosthesis is used, such as prosthesis 57A (FIG. 2A), the flap 58 remains unfolded as shown in FIG. 2A in which case the flap serves to contain prostheses 57 and 57A.

In addition to adjusting the underlay 14R in accordance with the nature and size of the prosthesis, the overlay 13 is adjusted. For example, if the wearer's left breast has not been removed, the left overlay panel 42 is adjusted with Velcro fasteners 50, 51 such that the edge 47 thereof is approximately aligned with the bra arm-hole edge 26. If the wearer's right breast has been removed the overlay section 60 of the right overlay 13R is adjusted using Velcro fasteners 61, 62, which are secured to the overlay section 60 and cup 16, respectively, to place the upper edge 63 thereof such that it covers any scar tissue or other chest disfigurement of the wearer resulting from removal of the right breast, as shown in FIGS. 2 and 2A.

Figure 2A:
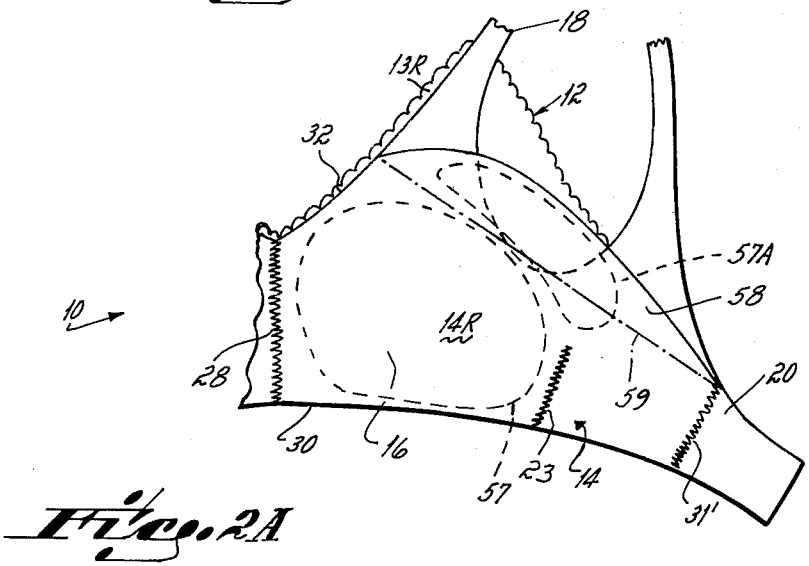
FIG. 2A is a rear elevational view of a portion of the embodiment of the invention depicted in FIG. 2 showing its use in connection with containment of multiple prostheses in a single pocket.

Thus, as is apparent from FIGS. 1, 2 and 2A, the underlay sections 14L and 14R with flaps 24 and 58 can accomodate natural breasts as well as varying size and shape prostheses, while the overlay sections 13L and 13R can be variably positioned depending upon the extent to which it is desired to hide scar tissue or other chest disfigurement resulting from a mastectomy.

The overlay 13 is constructed of stretchable material, either with elastic fibers, such as "stretch" lace and power knits; or with a non-elastic fiber, such as knits, tricots of all types, and materials made of stretchable yarns, for example, those with a high twist. The underlay 14 is preferably fabricated of a soft material, and may or may not be stretchable.

The embodiment depicted in FIG. 3 is identical to that depicted in FIGS. 1, 2 and 2A, except in two respects. First, the adjustable Velcro fasteners 50, 51 and 61, 62 for variably positioning the overlay panel sections 42 and 60 has been removed in the embodiment of FIG. 3. Second, the outer ends of the panels 42 and 60, instead of being permanently secured to the back sections 19 and 20 such as by stitching along line 31 and 31', as is the case in FIGS. 1, 2 and 2A, Velcro fasteners 66, 67 and 68, 69 are provided in FIG. 3. Specifically, mating Velcro strips 66 and 67 are secured to the bra back 19 and overlay strip 42, respectively, while Velcro strips 68 and 69 are secured to the bra back 20 and overlay section 60, respectively. The fasteners 66–69 of FIG. 3 facilitate adjustment of the location of the overlay panels 42 and 60 in much the same manner as Velcro fasteners 50, 51 and 61, 62 function in the embodiment of FIGS. 1, 2 and 2A.

The embodiment of FIG. 4 is identical to the embodiment of FIGS. 1, 2 and 2A except that the permanent connection along front center line 28 and at the junction line 43, 43' of the shoulder strap 17, 18 and cups 15, 16 have been substituted by Velcro fasteners. Specifically, in FIG. 4 complimentary Velcro strips 70 and 71 are secured to the front of the bra along line 28 and the inner surface of the central portion of the overlay 13. In addition, Velcro strips 72 and 73 have been secured to the strap 17 and the undersurface of the left overlay 13L, while Velcro strips 74 and 75 have been secured to the undersurface of the right overlay 13R and the strap 18. The use of Velcro in the manner noted in the embodiment of FIG. 4 permits the position of the left and right overlays 13L, 13R to be adjusted vertically depending upon the needs of the wearer. For example, note in FIG. 4 that a greater portion of the right arm-hole of the bra is covered than the left arm-hole.

The embodiment of FIG. 5 is identical to that shown in FIG. 4, except that Velcro fasteners have been added to the mid-portion of the overlay sections to enhance the adjustment capability. Specifically, Velcro straps 61 and 62 have been secured to the undersurface of the right overlay section 60 and to the outer surface of the right cup 16. Similar fasteners are provided on the left overlay section 42 and cup 15.

The embodiment of FIG. 6 is identical to the embodiment of FIG. 5 except that Velcro fasteners have been substituted for the permanent stitching along lines 31 and 31' of FIG. 5. Specifically, Velcro fasteners 77 and 78 have been secured to the outer surface of the right back section 20 and the undersurface of the right overlay section 60. Similarly, the left overlay section 42 is secured to the left back section 19.

Each of the embodiments of FIGS. 1–6 permit a wide range in variation of the left and right overlays 13L and 13R to accomodate varying needs of different uses for covering differing amounts of scar tissue and/or chest disfigurement resulting from a mastectomy. In addition, the embodiments of FIGS. 1–6 may, if desired, each facilitate containment of one or more prostheses of varying shapes in the pockets defined by the left and right underlays 14L and 14R and the left and right cups 15 and 16, respectively. Moreover, where the wearer does have one natural breast remaining, whether right or left, the mastectomy accessory 12 of this invention does not interfere with normal support and coverage of the remaining natural breast provided by the conventional bra 10 to which the mastectomy accessory of this invention has been added.

The embodiment of FIG. 7 is similar to the various embodiments of FIGS. 1–6 except that the overlay 13, including the left and right overlay sections 13L and 13R, are secured to the bra 10 with ties 80–84. Specifically, the left and right overlay sections 13L and 13R are secured to the straps 17 and 18 by ties 83 and 81, while the lower ends of the sections 42 and 60 are secured to the left and right back sections 19 and 20 by ties 84 and 80. The overlay 13 at the juncture of the left and right sections 13L and 13R is secured to the bra 10 in the region 28 thereof joining the cups 15 and 16 by the tie 82. In addition to ties as shown in FIG. 7, the overlay 13 of this version may be adjustably secured to the bra by means of small safety pins or other suitable means. Obviously, the overlay 13 of the embodiment of FIG. 7 can be adjusted in much the same manner as the overlays 13 of the previously described embodiments by variably positioning the ties 83 and 81 relative to the straps 17 and 18. An advantage of the overlay 13 of FIG. 7 is that it can be added to a conventional bra without stitching or addition of the permanent fasteners. Although not shown, the embodiment of FIG. 7, like the embodiments of FIGS. 1–6, may be provided with the pocket-establishing underlay 14.

The four embodiments of FIGS. 8, 9, 10 and 11 differ from the embodiments of FIGS. 1–7 in that instead of inverted "V" overlays 13L and 13R positioned over each of the cups 16 and 15, a single band of stretch material 90 is provided over the right cup 16 and a single band of stretch material (not shown) is provided over the left cup. In the embodiment of FIG. 8, the band 90 is permanently secured at its inner end by stitching or the like along the edge 93 of the right cup 16 as well as along its opposite edge 95 to the right back section 20 of the bra 10. A Velcro strip 97 secured to the outer surface of the right cup 16 cooperates with a Velcro strip 98 secured to the undersurface of the band 90 to permit the position of the band 90 relative to the arm-hole edge 26' to be adjusted. The left side is not shown in its entirety but it should be understood that a band similar to band 90 is secured to the left cup 15 and provided with Velcro fasteners in a manner similar to that of band 90. Depending upon the extent, if any, of scar tissue or chest disfigurement of the wearer, the bands 90 can be variably positioned with respect to the arm-hole in much the same fashion as the overlays 13L and 13R of the embodiments of FIGS. 1–7.

The embodiment of FIG. 9 is similar to the embodiment of FIG. 8, except that the Velcro fasteners 97, 98 of the embodiment of FIG. 8 have been omitted, and the stitching along outer edge 95 of the band 90 of the embodiment of FIG. 8 has been replaced by Velcro fasteners 100 and 101. Specifically, Velcro fastener 100 is secured to the outside surface of cup 16 and cooperates with Velcro fastener 101 secured to the inside surface of the end of band 90 to facilitate variable relative positioning of the band 90 with respect to the arm-hole edge 26'.

The embodiment of FIG. 10 is similar to the embodiment of FIG. 9, except that the permanent stitching of the band 90 along edge 93 has been substituted with Velcro strips 105 and 106, and the Velcro fastener 100, 101 of FIG. 9 has been replaced by permanent stitching 107. By adjustably positioning the Velcro 105 secured to the cup 16 and the Velcro 106 secured to the band 90, the band 90 can be raised or lowered with respect to the arm-hole edge 26' to cover more or less of the underarm region of the wearer.

The embodiment of FIG. 11 is identical to the FIG. 10 embodiment, except that the permanent connection of band 90 along outer edge 95 is replaced by Velcro fasteners 110 and 111 secured to the right back 20 of the bra 10 and the inner surface of the outer end of the band 90. Adjustment of Velcro fasteners 110, 111 and 105, 106 at opposite ends of band 90 permits varying amounts of the wearer's chest and underarm region to be covered.

While fasteners of the Velcro type have been described, other types of vertically adjustable fasteners can be used, such as hooks and eyelets, snaps, etc.

In each of the embodiments of FIGS. 8–11 an underlay 14 may, if desired, be provided which is identical in structure and function to the underlay 14 provided in the embodiment of FIGS. 1–7.

What is claimed is:

1. A mastectomy bra comprising:

first and second interconnected cup-containing front panels adapted, when the bra is worn, to be positioned over the wearer's right and left breast regions, respectively, first and second rear panels connected to and extending rearwardly from said first and second front panels, respectively, to at least the wearer's back and adapted, when the bra is worn, to be positioned under the right and left arms of the wearer, respectively, said front panels and said rear panels having an upper edge, an overlay located to overlie a substantial portion of the upper edge of at least one front panel and associated connected rear panel, adjustable fastening means interconnecting said overlay and said at least one front panel and associated connected rear panel for fastening said overlay to extend above said upper edge of said at least one front panel and associated connected rear panel varying amounts depending upon the amount of scar tissue and/or other chest disfigurement to be covered, and an underlay positioned to underlie a substantial portion of said at least one front panel and associated connected rear panel, said underlay being secured to said at least one front panel and associated connected rear panel along substantially its entire periphery except for the upper edge thereof, said upper edge of said underlay in combination with the adjacent upper edge of said at least one front panel and associated connected rear panel establishing an opening, said underlay and said at least one front panel and associated connected rear panel jointly establishing a pocket for containing at least one prosthesis insertable therein through said opening.

2. The mastectomy bra of claim 1 wherein said overlay is configured to overlie the upper edge of both said front panels and associated connected rear panels, and wherein said underlay is configured to underlie both said front panels and associated connected rear panels.

3. The mastectomy bra of claim 1 wherein said at least one front panel is configured to contain and support a normal breast, and wherein said overlay is configured to extend above said upper edge of said at least one front panel and associated connected rear panel beyond the location of a normal breast.

4. The mastectomy bra of claim 1 wherein said overlay is only adjustably connected to said at least one front panel and associated connected rear panel to facilitate a maximum range of adjustment relative to said upper edge of said at least one front panel and associated connected rear panel.

5. The mastectomy bra of claim 1 wherein said overlay is adjustably connected at at least one point to said at least one front panel and associated connected rear panel and is permanently connected at at least a second point to said at least one front panel and associated connected rear panel.

6. The mastectomy bra of claim 1 wherein said overlay is elongated having opposite ends, one of said ends being connected to the upper region of said at least one front panel and the other of said ends being connected to said at least one associated connected rear panel at a point rearwardly of the wearer's arm when the bra is worn, and wherein said adjustable fastening means includes a fastener interconnecting said at least one front panel and said overlay at a point intermediate said ends.

7. The mastectomy bra of claim 2 wherein said overlay has a generally M-shape including four elongated bands, two of said bands each connected at one end to said front panels proximate their point of interconnection and each connected at the other end to different front panels above the cup therein, the other two of said bands each being connected at one end to different front panels above the cup therein and each connected at the other end to different rear panels at points rearwardly of the wearer's arms.

8. The mastectomy bra of claim 2 wherein said overlay includes two elongated bands, said bands at one end each being connected to different front panels above the cup therein and at the other end each being connected to different rear panels at points rearwardly of the wearer's arms.

9. A mastectomy bra comprising:
first and second interconnected cup-containing front panels adapted, when the bra is worn, to be positioned over the wearer's right and left breast regions, respectively,
first and second rear panels connected to and extending rearwardly from said first and second front panels, respectively, to at least the wearer's back and adapted, when the bra is worn, to be positioned under the right and left arms of the wearer, respectively,
said front panels and said rear panels having an upper edge,
an overlay located to overlie a substantial portion of the upper edge of at least one front panel and associated connected rear panel, and
adjustable fastening means interconnecting said overlay and said at least one front panel and associated connected rear panel for fastening said overlay to extend above said upper edge of said at least one front panel and associated connected rear panel varying amounts depending upon the amount of scar tissue and/or other chest disfigurement to be covered.

10. The mastectomy bra of claim 9 wherein said overlay is configured to overlie the upper edge of both said front panels and associated connected rear panels.

11. The mastectomy bra of claim 9 wherein said at least one front panel is configured to contain and support a normal breast, and wherein said overlay is configured to extend above said upper edge of said at least one front panel and associated connected rear panel beyond the location of a normal breast.

12. The mastectomy bra of claim 9 wherein said overlay is only adjustably connected to said at least one front panel and associated connected rear panel to facilitate a maximum range of adjustment relative to said upper edge of said at least one front panel and associated connected rear panel.

13. The mastectomy bra of claim 9 wherein said overlay is adjustably connected at at least one point to said at least one front panel and associated connected rear panel and is permanently connected at at least a second point to said at least one front panel and associated connected rear panel.

14. The mastectomy bra of claim 9 wherein said overlay is elongated having opposite ends, one of said ends being connected to the upper region of said at least one front panel and the other of said ends being connected to said at least one associated connected rear panel at a point rearwardly of the wearer's arm when the bra is worn, and wherein said adjustable fastening means includes a fastener interconnecting said at least one front panel and said overlay at a point intermediate said ends.

15. The mastectomy bra of claim 10 wherein said overlay has a generally M-shape including four elongated bands, two of said bands each connected at one end to said front panels proximate their point of interconnection and each connected at the other end to different front panels above the cup therein, the other two of said bands each being connected at one end to different front panels above the cup therein and each connected at the other end to different rear panels at points rearwardly of the wearer's arms.

16. The mastectomy bra of claim 10 wherein said overlay includes two elongated bands, said bands at one end each being connected to different front panels above the cup therein and at the other end each being connected to different rear panels at points rearwardly of the wearer's arm.

17. A mastectomy accessory for converting into a mastectomy bra a bra of conventional design having first and second interconnected cup-containing front panels adapted to overlie the wearer's right and left breast regions, respectively, and first and second rear panels connected to and extending rearwardly from said first and second front panels, respectively, to at least the wearer's back and adapted to be positioned under the right and left arms, both said front and rear panels having an upper edge, said accessory comprising:
a detachable overlay located to overlie a substantial portion of the upper edge of said front panels and associated connected rear panels, and
adjustable fastening means permanently secured to said overlay and connectable to said panels for adjustably and temporarily fastening said overlay to extend above said upper edge of said panels varying amounts depending upon the amount of scar tissue and/or other chest disfigurement to be covered.

18. The mastectomy accessory of claim 17 wherein said adjustable fastening means includes a plurality of individual tie members permanently secured to said overlay at spaced points for temporarily securing said overlay to different spaced points of said bra.

* * * * *